(12) United States Patent
Frankland et al.

(10) Patent No.: US 9,011,490 B2
(45) Date of Patent: Apr. 21, 2015

(54) SUTURE RETENTION DEVICE

(75) Inventors: Gregory A. Frankland, Bloomington, IN (US); Scott K. Philhower, Bloomington, IN (US); Michael W. Hardert, Bloomington, IN (US)

(73) Assignee: Cook Medical Technologies, LLC, Bloomington, IN (US)

( * ) Notice: Subject to any disclaimer, the term of this patent is extended or adjusted under 35 U.S.C. 154(b) by 622 days.

(21) Appl. No.: 13/408,330

(22) Filed: Feb. 29, 2012

(65) Prior Publication Data

US 2012/0226310 A1    Sep. 6, 2012

Related U.S. Application Data

(60) Provisional application No. 61/448,840, filed on Mar. 3, 2011.

(51) Int. Cl.
| | |
|---|---|
| *A61B 17/04* | (2006.01) |
| *A61B 17/02* | (2006.01) |
| A61B 17/00 | (2006.01) |
| A61B 19/00 | (2006.01) |

(52) U.S. Cl.
CPC ......... *A61B 17/0281* (2013.01); *A61B 17/0401* (2013.01); *A61B 17/0487* (2013.01); *A61B 2017/00407* (2013.01); *A61B 2017/0417* (2013.01); *A61B 2017/0448* (2013.01); *A61B 2019/4842* (2013.01)

(58) Field of Classification Search
CPC ..................... A61B 17/0401; A61B 17/06166; A61B 17/0487; A61L 31/08; A61L 31/16; A61L 2300/404; A61L 2300/414; Y10S 97/847
USPC ......... 606/232, 228, 224, 225, 226, 227, 229, 606/230, 231, 139, 148, 153, 151, 144, 200, 606/192, 194, 213, 216, 217; 24/134 N, 24/136 R, 115 H, 134 A, 134 L, 115 G, 24/115 R, 466, 591.1, 598.5, 601.3, 632, 24/634, 635, 648, 649, 657, 658; 424/423; 428/375, 378; 977/847; 604/264, 206, 604/533, 538, 326, 921
See application file for complete search history.

(56) References Cited

U.S. PATENT DOCUMENTS

| | | |
|---|---|---|
| 4,750,492 A | 6/1988 | Jacobs |
| 5,345,657 A | 9/1994 | Shimizu |
| 5,514,159 A | 5/1996 | Matula et al. |
| 5,653,711 A | 8/1997 | Hayano et al. |
| 5,666,699 A | 9/1997 | Takahashi |
| 5,919,208 A | 7/1999 | Valenti |
| 7,517,357 B2 | 4/2009 | Abrams et al. |
| 7,837,710 B2 | 11/2010 | Lombardo et al. |

FOREIGN PATENT DOCUMENTS

GB    2 066 891 A    1/1981

*Primary Examiner* — Jocelin Tanner
(74) *Attorney, Agent, or Firm* — Brinks Gilson & Lione

(57) ABSTRACT

A suture retention device is provided for retaining a suture. The device includes a body with a channel and two retention members within the channel. The retention members are movable between an unlocked state to a locked state in which the suture is restrained with respect to the body.

20 Claims, 11 Drawing Sheets

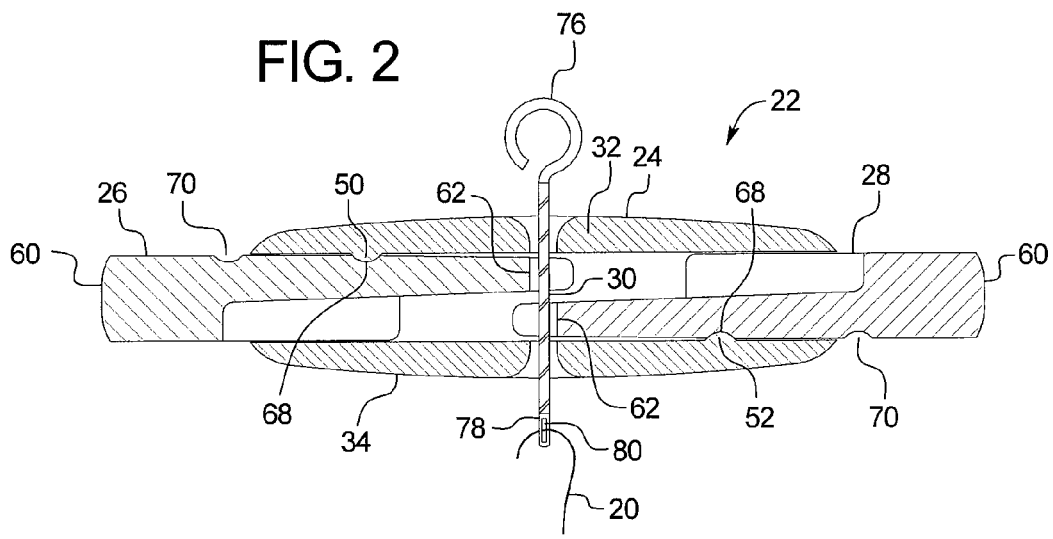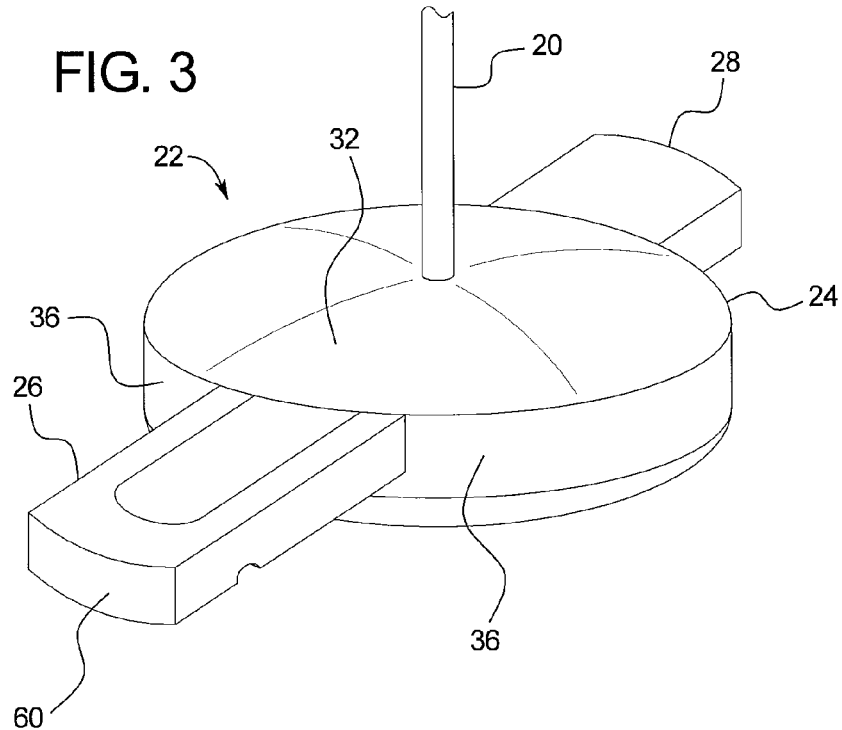

SUTURE RETENTION DEVICE

This application claims priority to U.S. Provisional Application No. 61/448,840, filed Mar. 3, 2011, which is hereby incorporated by reference herein.

BACKGROUND

The present invention relates generally to medical devices and more particularly to a device to retain a suture.

Suture retention devices are sometimes used in percutaneous direct feeding methods to secure a tethering suture to the exterior of a patient. In such methods, a gastrostomy or gastrojejunostomy tube is inserted through a patient's abdominal wall and stomach or jejunum wall to provide nutrients directly to the gastrointestinal tract. A wide range of medical diseases and conditions may require a patient to be fed by this type of feeding method, such as esophageal cancer, anorexia and multiple sclerosis.

In order to maintain the wall of the stomach or jejunum in the proper location for feeding through the gastrostomy or gastrojejunostomy tube, anchors may be placed against the interior wall of the stomach or jejunum. Tethering sutures attached to the anchors may pass through the wall of the stomach or jejunum and the abdominal wall, and the loose ends of the sutures may be secured against the exterior of the patient's abdominal wall with various types of suture retention devices. As a result, the stomach or jejunum can be pulled against the interior surface of the abdominal wall so that the depth of the stomach or jejunum is precisely located. The lateral position of the stomach or jejunum is also controlled since the stomach or jejunum is prevented from moving relative to the abdominal wall.

Although suture retention devices are particularly useful in direct feeding medical procedures, suture retention devices may also be used in other medical procedures as well.

SUMMARY

A suture retention device is described. The device has a body and at least first and second retention members. The retention members move within a channel through the body between an unlocked state and a locked state. In the unlocked state, a suture can be threaded through a pair of coaxial holes in the body. In the locked state, the suture is forced into a zig-zag configuration within the channel by the retention members to restrain the suture with respect to the body. The inventions herein may also include any other aspect described below in the written description, the claims, or in the attached drawings and any combinations thereof.

BRIEF DESCRIPTION OF SEVERAL VIEWS OF THE DRAWINGS

The invention may be more fully understood by reading the following description in conjunction with the drawings, in which:

FIG. 2 is a cross-sectional view of a suture retention device, showing a retention wire installed in the device;

FIG. 3 is a perspective view of the suture retention device, showing a suture extending through the device;

DETAILED DESCRIPTION

Figure 1:
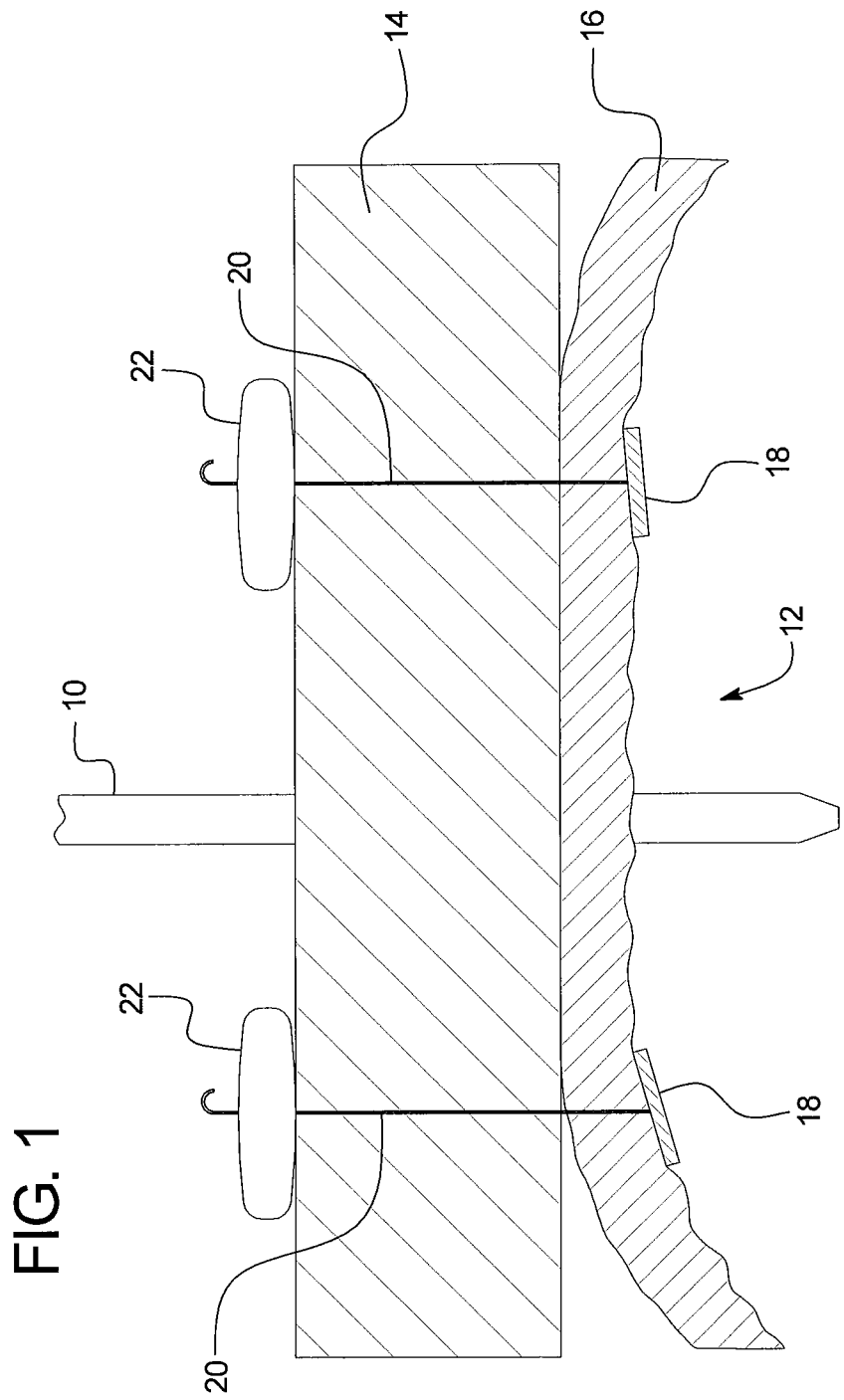
FIG. 1 is a cross-sectional view of a feeding tube inserted into a patient's stomach through the abdominal wall with anchors and suture retention devices retaining the stomach against the abdominal wall.

Referring now to the figures, and particularly to FIG. 1, a feeding tube 10 is shown inserted into a patient's stomach 12 through the abdominal wall 14. The stomach wall 16 is retained against the interior surface of the abdominal wall 14 with anchors 18 that are attached to tethering sutures 20. The sutures 20 pass through the stomach wall 16 and the abdominal wall 14 and are secured to the exterior surface of the abdominal wall 14 with suture retention devices 22. Typically, three sets of anchors 18, sutures 20 and retention devices 22 may be used in a triangular arrangement with the feeding tube 10 located in the center of the triangle formed by the retention devices 22. This arrangement is useful because it provides an identifiable region to place the feeding tube 10 where the stomach wall 16 is firmly located against the interior of the abdominal wall 14.

The stomach 12 may be anchored against the abdominal wall 14 by insufflating the stomach 12 with air using a nasogastric tube. Then, a needle may be used to puncture through the abdominal wall 14 and the stomach wall 16. The anchor 18 with a suture 20 attached to the center of the anchor 18 may then be pushed through the needle and released into the stomach 12 with a guide wire. The needle is then withdrawn from the stomach 12, abdominal wall 14 and the loose end of the suture 20. A suture retention device 22 may then be placed on the loose end of the suture 20. In order to properly locate the stomach 12 against the interior of the abdominal wall 14, the suture 20 is pulled to draw the stomach wall 16 against the abdominal wall 14 and the suture retention device 22 is pushed against the exterior of the abdominal wall 14. Once the appropriate tension is applied to the suture 20 and the suture retention device 22, the suture retention device 22 is locked to hold the suture 20 in place and maintain a fixed distance between the anchor 18 and the suture retention device 22. This process may then be repeated to place and retain any remaining anchors 18.

Figure 4:
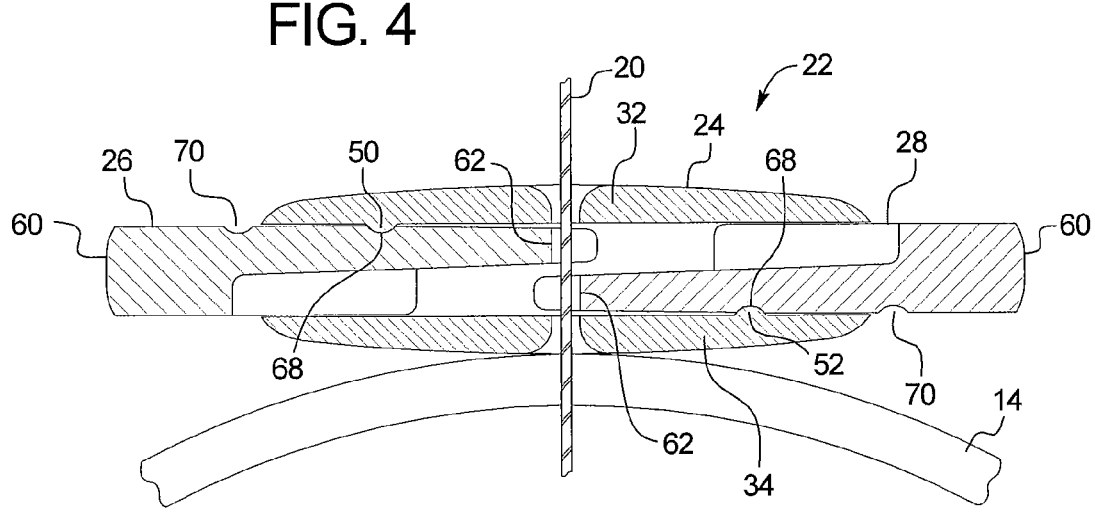
FIG. 4 is a cross-sectional view of the suture retention device, showing the suture extending through the device in the unlocked state.

As shown in FIGS. 2-5, the suture retention device 22 includes a body 24, a first retention member 26, and a second retention member 28. As shown in FIG. 2, the suture retention device 22 is provided to the physician in an unlocked state. The suture retention device 22 may also be provided with a retention wire 30 as described further below. As shown in FIGS. 3 and 4, the physician threads a suture 20 through the suture retention device 22 while the device 22 is in the unlocked state. Then, when the suture 20 and retention device 22 are properly positioned, the suture retention device 22 is locked by pushing the first and second retention members 26, 28 into the body 24 of the device 22.

Figure 6:
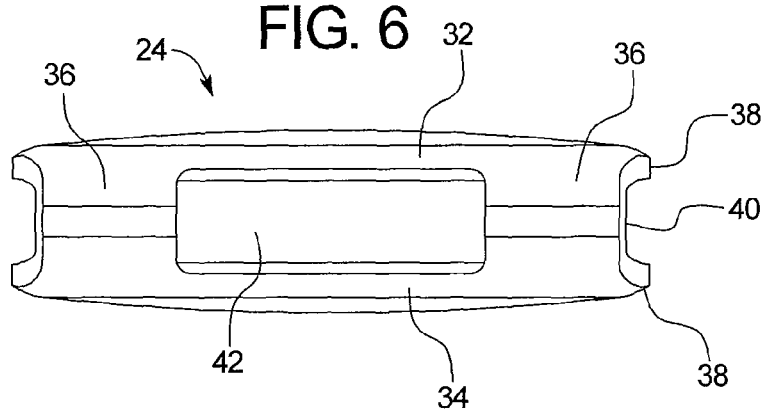
FIG. 6 is an end view of the body of the suture retention device.
Figure 7:
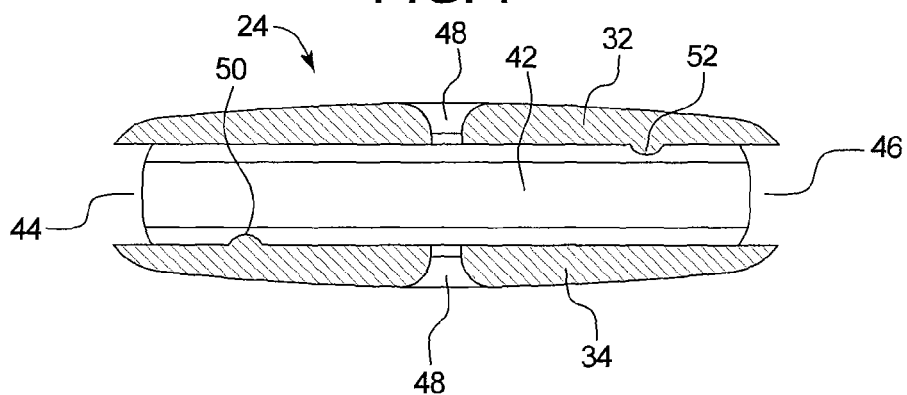
FIG. 7 is a side cross-sectional view of the body.
Figure 8:
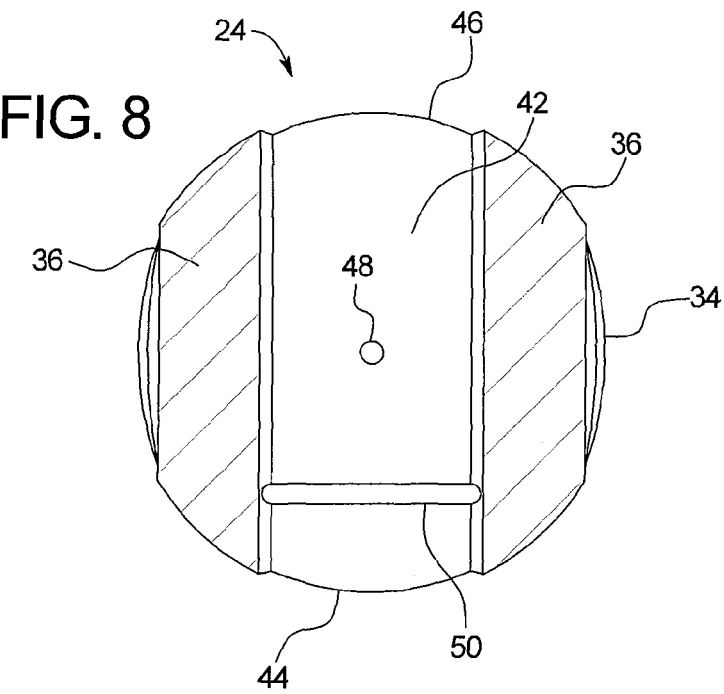
FIG. 8 is a top cross-sectional view of the body.
Figure 9:
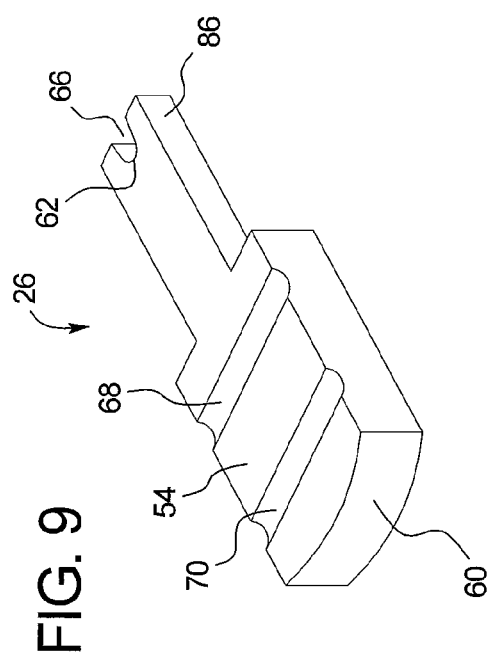
FIG. 9 is a perspective view of one of the retention members of the suture retention device.

As shown in FIGS. 6-8, the body 24 of the suture retention device 22 has a top wall 32, a bottom wall 34 and side walls 36 that connect the top and bottom walls 32, 34 together. Preferably, the body 24 is made from an injection molded polymer, such as polyethylene, that allows the body 24 to flex sufficiently to allow the first and second retention members 26, 28 to move through the body 24 between the unlocked and locked states described further below. The overall size of the body 24 is preferably about ½" in diameter, or less than 1" in diameter, and about 0.150" thick, or less than 0.5" thick. As shown in FIG. 7, the exterior of the top and bottom walls 32, 34 is also preferably smoothly contoured to provide smooth contact with the patient's skin and to avoid snagging the top of the suture retention device 22. As shown in FIG. 6, the exterior sides of the body 24 may be provided with lips 38 that provide a smooth edge to the suture retention device 22. The lips 38 may also extend outward from a recessed side surface 40 where the mold can be gated so that the remnant of the gate can be protected by the lips 38. The body 24 further includes a channel 42 between the top and bottom walls 32, 34 that extends through the body 24 from one side opening 44 to another side opening 46 at the opposite side of the body 24. Although a single side wall 36 may be used, two side walls 36 preferably enclose the channel 42 to define a width between the side walls 36 that corresponds to the width of the first and second retention members 26, 28 so that the side walls 36 guide the first and second retention members 26, 28 as they are pushed from the unlocked state to the locked state. A pair of coaxial holes 48 extend through the top and bottom walls 32, 34 so that the coaxial holes 48 are in communication with the exterior of the body 24 and the channel 42 through the body 24. Preferably, the coaxial holes 48 are located in the center of the body 24 and the channel 42 both laterally and longitudinally. The diameter of the coaxial holes 48 may be at least twice as large as the tethering suture 20 so that the suture 20 may be easily threaded through the coaxial holes 48. For example, with a suture 20 that is about 0.008" in diameter, the coaxial holes 48 may have a diameter of at least 0.016", or more preferably about 0.025". The channel 42 includes a pair of protrusions 50, 52, or locking features 50, 52, on opposite sides of the coaxial holes 48 between the coaxial holes 48 and the side openings 44, 46. The protrusions 50, 52 are preferably ridges 50, 52 that extend across the channel 42. The protrusions 50, 52 are located along the inner surfaces of the channel 42. For example, the first protrusions 50 may be located on the inner surface of the bottom wall 34 between the coaxial holes 48 and the first side opening 44, and the second protrusions 52 may be located on the inner surface of the top wall 32 between the coaxial holes 48 and the second opposite side opening 46. However, the protrusions 50, 52 may also be located on other inner surfaces of the channel 42 and/or may be reversed like FIG. 2.

As shown in FIGS. 9-12, the first and second retention members 26, 28 include a top surface 54, a first bottom surface 56, a second bottom surface 58 and an end surface 60. Preferably, the first and second retention members 26, 28 are identical to each other in order to simplify manufacturing. However, if desired, the first and second retention members 26, 28 may be different from each other. The first and second retention members 26, 28 may be injection molded from a polymer, such as polyethylene, like the body 24 or may be made from a different material.

Figure 11:
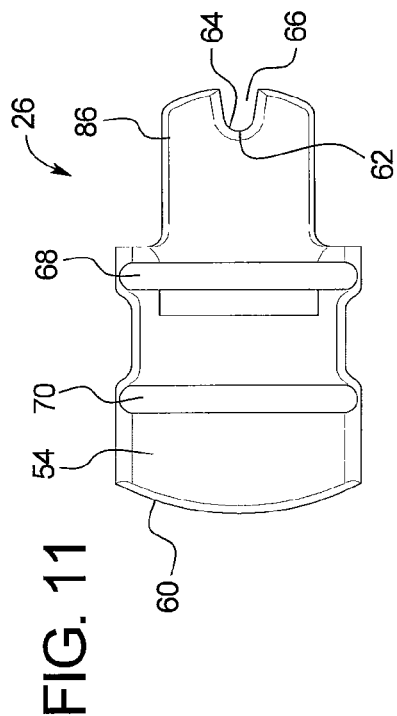
FIG. 11 is a top view of the retention member.
Figure 12:
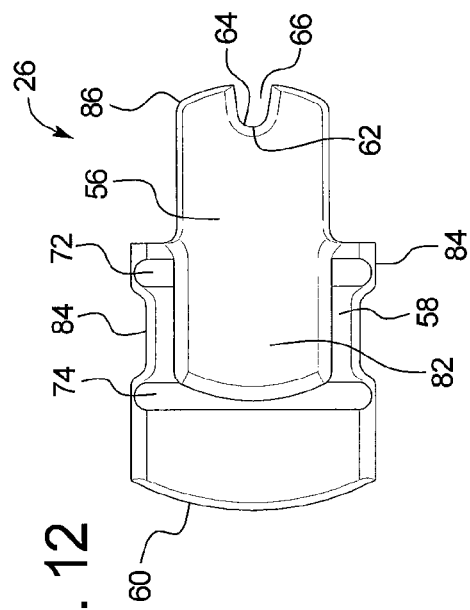
FIG. 12 is a bottom view of the retention member.

Each of the first and second retention members 26, 28 also includes a side surface 62 near the end of the retention members 26, 28 away from the end surface 60. As described below, the side surface 62 is suitable for engaging a suture 20 threaded through the coaxial holes 48. Thus, the side surfaces 62 are laterally aligned with the coaxial holes 48. The side surface 62 extends through the thickness of each of the first and second retention members 26, 28 between the top surface 54 and the first bottom surface 56. As shown in FIGS. 11-12, the side surface 62 may be a portion of a circular surface 64 at the closed side of an open-ended slot 66 at the opposite end from the end surface 60. Preferably, the circular surface 64 is in alignment with the coaxial holes 48 in the unlocked state and has a diameter at least twice the size of the suture 20. For example, with a suture 20 that is about 0.008" in diameter, the circular surface 64 may have a diameter along the curved portion of at least 0.016", or more preferably about 0.025". Alternatively, the side surface 62 may be a portion of a hole extending through the retention member 26, 28.

Figure 5:
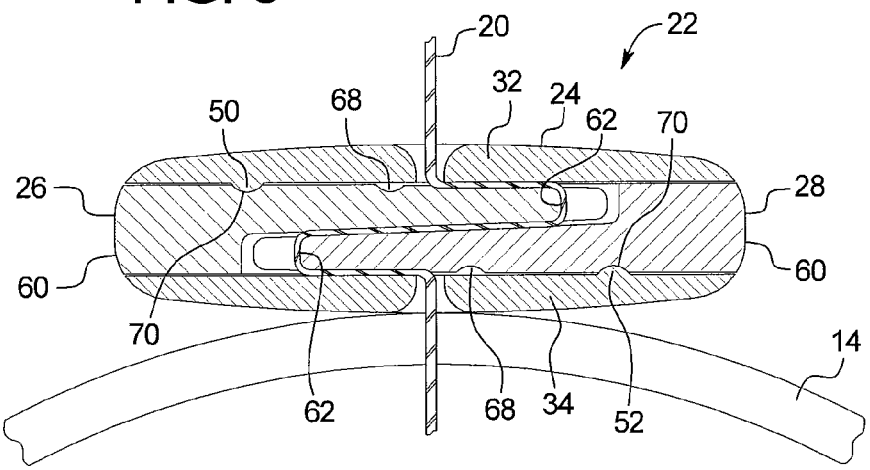
FIG. 5 is a cross-sectional view of the suture retention device, showing the suture extending through the device in the locked state.
Figure 10:
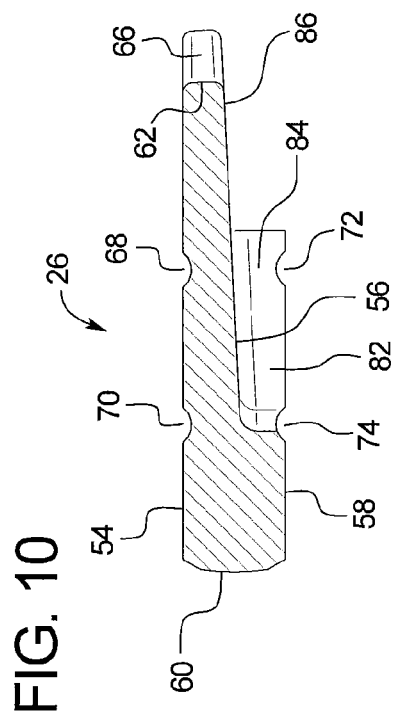
FIG. 10 is a side cross-sectional view of the retention member.

The first and second retention members 26, 28 also each include a pair of recesses 68, 70, or third 68 and fourth 70 locking features, on either the top surface 54 or the second bottom surface 58. The recesses 68, 70 are preferably grooves 68, 70 that extend across each of the first and second retention members 26, 28. The recesses 68, 70 are longitudinally spaced apart from each other so that the first recess 68 corresponds to the unlocked state where the first recess 68 and the body protrusion 50, 52 receive each other, and the second recess 70 corresponds to the locked state where the second recess 70 and the body protrusion 50, 52 receive each other. As shown in FIGS. 4-5, the first and second recesses 68, 70 are preferably located on the top surfaces 54 of the first and second retention members 26, 28. As shown in FIGS. 10 and 12, the first and second retention members 26, 28 may also have corresponding recesses 72, 74 on the opposite side from the first and second recesses 68, 70. For example, the corresponding recesses 72, 74 may be on the second bottom surface 58. The corresponding recesses 72, 74 may be at the same longitudinal position as the first and second recesses 68, 70 so that the corresponding recesses 72, 74 receive the protrusions 50, 52 of the body 24 in the unlocked and locked states in place of the first and second recesses 68, 70 when the first and second retention members 26, 28 are incorrectly installed within the channel 42. For example, with reference to FIG. 2, this may be useful if the installer inadvertently reverses the first and second retention members 26, 28 so that the top surface 54 of the first retention member 26 engages the inner surface of the bottom wall 34 of the body 24 and the top surface 54 of the second retention member 28 engages the inner surface of the top wall 32 of the body 24.

As shown in FIGS. 2 and 4, in the unlocked state, the first retention member 26 extends through the first side opening 44 of the body 24. The top surface 54 of the first retention member 26 engages the inner surface of the top wall 32 of the body 24, and the second bottom surface 54 of the first retention member 26 engages the inner surface of the bottom wall 34. The first recess 68 of the first retention member 26 receives the first protrusion 50 of the body 24. The end surface 60 of the first retention member 26 is positioned outside of the channel 42, and the side surface 62 of the first retention member 26 is positioned between the end surface 60 of the first retention member 26 and the coaxial holes 48 of the body 24. Similarly, the second retention member 28 extends through the second opposite side opening 46 of the body 24. The top surface 54 of the second retention member 28 engages the inner surface of the bottom wall 34 of the body 24, and the second bottom surface 58 of the second retention member 28 engages the inner surface of the top wall 32. The first recess 68 of the second retention member 28 receives the second protrusion 52 of the body 24. The end surface 60 of the second retention member 28 is positioned outside of the channel 42, and the side surface 60 of the second retention member 28 is positioned between the end surface 60 of the second retention member 28 and the coaxial holes 48 of the body 24. The description of "top" and "bottom" throughout this description is with reference to the drawings to assist in understanding the described structure. However, the described structures may be reversed or modified as desired. For example, the entire suture retention device 22 or portions thereof could be flipped over so that the described top surface 54 becomes effectively a bottom surface. Likewise, the protrusions 50, 52 on the body 24 could be modified to be recesses, while the recesses 68, 70 on the retention members 26, 28 could be modified to be protrusions.

As shown in FIG. 2, in the unlocked state, it may be preferable to provide a retention wire 30 extending through the coaxial holes 48 to prevent the first and second retention members 26, 28 from being prematurely pushed to the locked state. The retention wire 30 may have a first end 76 that is larger in size than the coaxial holes 48 that is positioned above the top wall 32 of the body 24. The retention wire 30 may also have a second end 78 that is smaller in size than the coaxial holes 48 that is positioned below the bottom wall 34 of the body 24. Thus, the retention wire 30 is withdrawable by pulling the first end 76 away from the top wall 32 of the body 24 but is not withdrawable by pulling the second end 78 away from the bottom wall 34. The second end 78 may also have a cross hole 80 extending through the second end 78 below the bottom wall 34 of the body 24. The cross hole 80 may be useful as shown in FIG. 2 for threading the suture 20 through, which can then be threaded through the coaxial holes 48 in the suture retention device 22 when the retention wire 30 was withdrawn.

As shown in FIG. 5, in the locked state, the first and second retention members 26, 28 are slid through the channel 42 towards each other by pushing the end surfaces 60 of the first and second retention members 26, 28 toward the side openings 44, 46 of the body 24 so that the first recesses 68 of the first and second retention members 26, 28 disengage from the protrusions 50, 52 of the body 24. The second recesses 70 of the first and second recesses 26, 28 then receive the protrusions 50, 52 of the body 24 to lock the first and second retention members 26, 28. As a result, the side surfaces 62 of the first and second retention members 26, 28 pass by the coaxial holes 48 of the body 24 and pull the suture 20 extending through the coaxial holes 48 through the channel 42 and away from the coaxial holes 48. Portions of the first and second retention members 26, 28 also overlie each other with the first bottom surfaces 56 of the first and second retention members 26, 28 facing each other within the channel 42 at the coaxial holes 48. Each of the first and second retention members 26, 28 may also have a recessed portion 82 defined by side walls 84 between the end surface 60 and an end portion 86 that is opposite from the end surface 60. The side walls 84 may define the second bottom surfaces 58 of the first and second retention members 26, 28. Thus, the end portions 86 of each retention member 26, 28 may extend into the recessed portion 82 of the other retention member 26, 28 in the locked position. It may be preferable for the end surfaces 60 to be generally aligned with the side openings 44, 46 of the body 24 in the locked state so that the suture retention device 22 cannot be readily unlocked since the first and second retention members 26, 28 cannot be easily grasped in the locked state. As shown in FIG. 5, the suture 20 is forced along a zig-zag path within the suture retention device 22. As a result, the suture 20 becomes restrained within the device 22 and cannot be readily pulled through the coaxial holes 48 due to friction between the suture 20 and the first and second retention members 26, 28 and the body 24.

Figure 13:
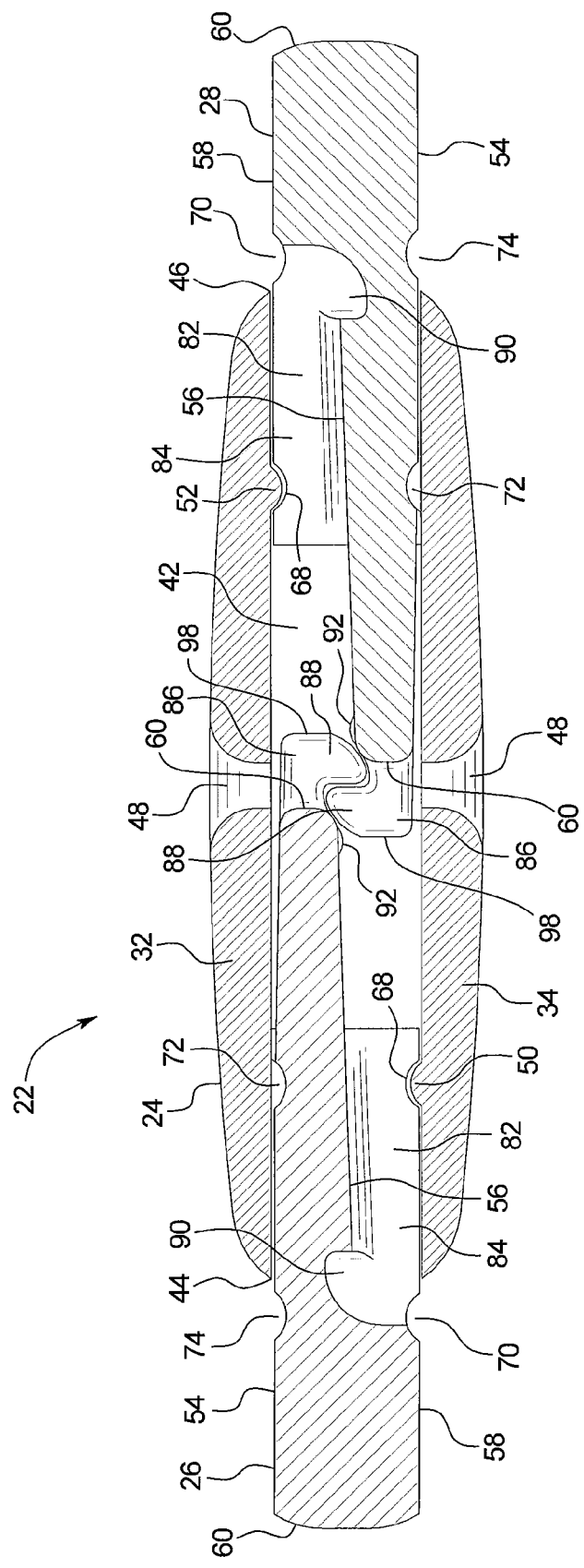
FIG. 13 is a cross-sectional view of another embodiment of the suture retention device, showing the device in the unlocked state.
Figure 14:
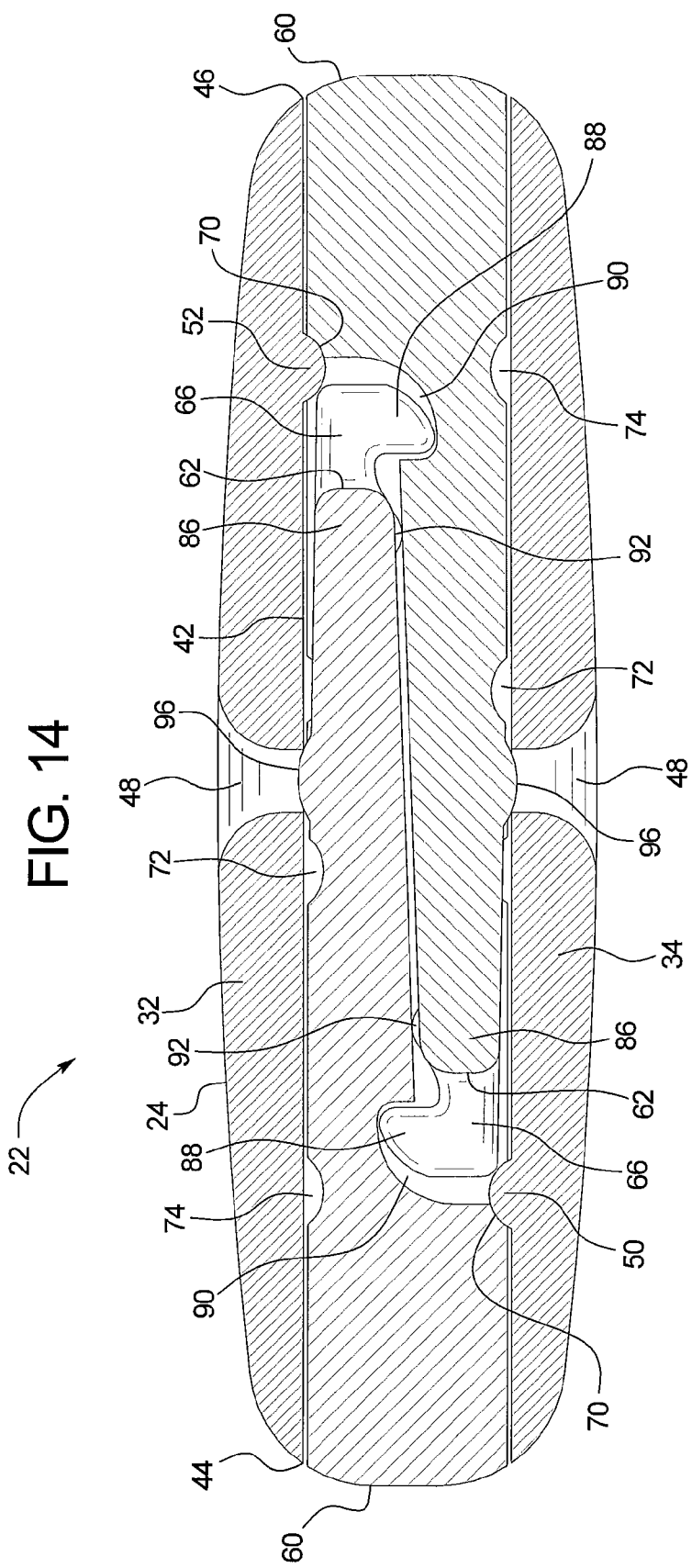
FIG. 14 is a cross-sectional view of the suture retention device, showing the device in the locked state.

As shown in FIG. 13, each of the first and second retention members 26, 28 may also be provided with a hook 88 along the end portion 86 opposite from the end surface 60. The hook 88 of the first retention member 26 extends toward the inner surface of the bottom wall 34 of the body 24 and the hook 88 of the second retention member 28 extends toward the inner surface of the top wall 32 of the body 24. As a result, the hooks 88 engage each other in the unlocked state to prevent the first and second retention members 26, 28 from being pulled out of the body 24. As shown in FIG. 14, each of the first and second retention members 26, 28 may also be provided with a recess 90 in the first bottom surface 56 that receives the hook 88 from the other retention member 26, 28 in the locked state. As a result, the hook 88 latches into the recesses 90 to increase the force needed to unlock the suture retention device 22.

Figure 15:
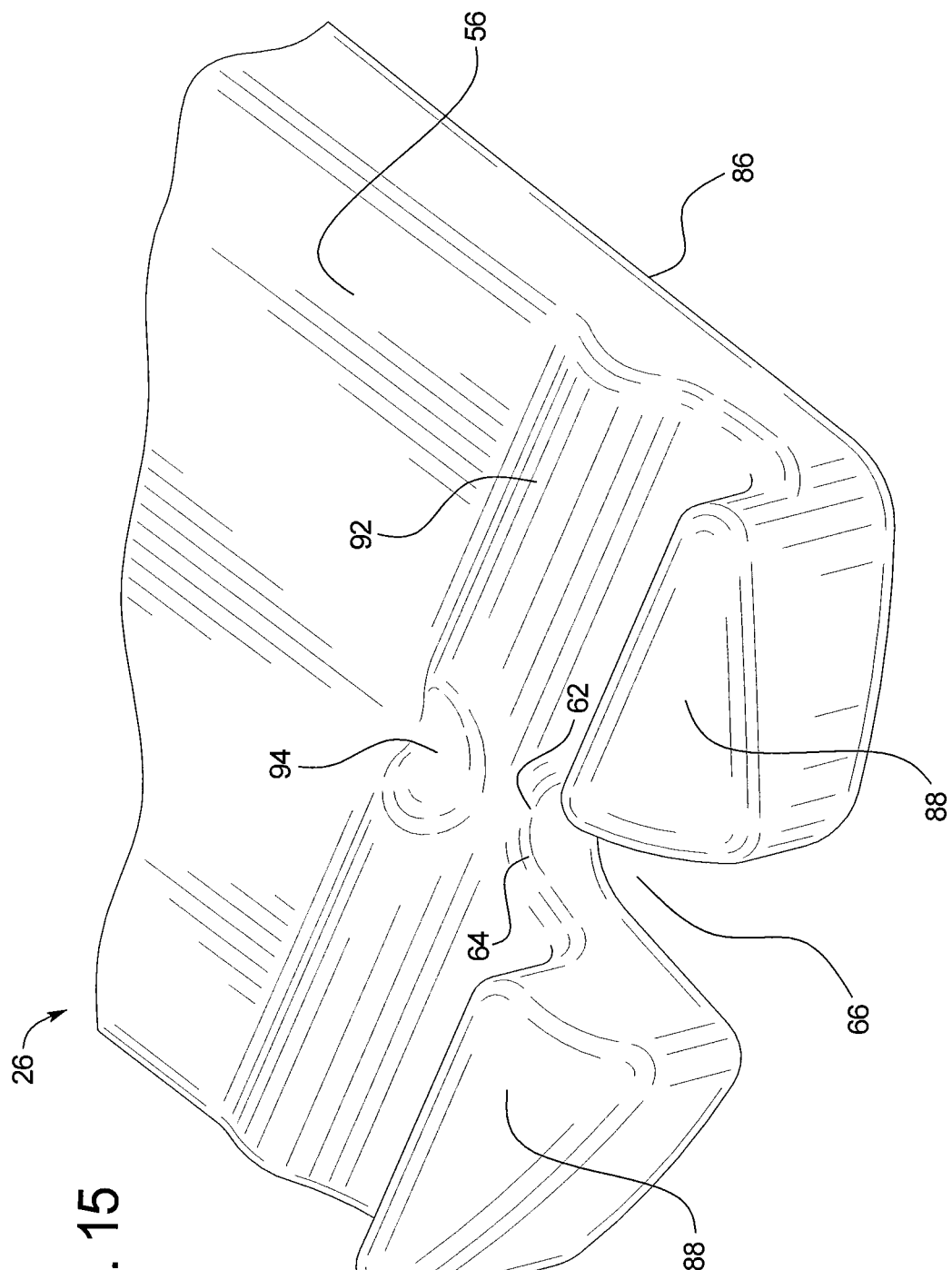
FIG. 15 is a perspective view of the bottom end portion of the retention member of FIGS. 13-14.

As shown in FIG. 13, each of the first and second retention members 26, 28 may also include a protrusion 92 that extends from the first bottom surfaces 56 of the first and second retention members 26, 28. As a result, the protrusions 92 force the hook 88 of the first and second retention members 26, 28 to flex over the protrusions 92 when the first and second retention members 26, 28 are pushed toward the locked state. This may be useful to increase the force required to push the first and second retention members 26, 28 out of the unlocked state and toward the locked state. As shown in FIG. 15, each of the protrusions 92 may be a ridge that extends across the retention members 26, 28. The ridge 92 may also be provided with a recess 94 extending through each ridge 92 that is laterally aligned with the coaxial holes 48 to provide clearance for the suture 20.

As shown in FIG. 14, each of the first and second retention members 26, 28 may also be provided with a protrusion 96 extending from the top surface 54 of each retention member 26, 28. Each of the protrusions 96 may extend at least partially into one of the coaxial holes 48 in the locked state to increase the force needed to unlock the suture retention device 22.

Figure 16:
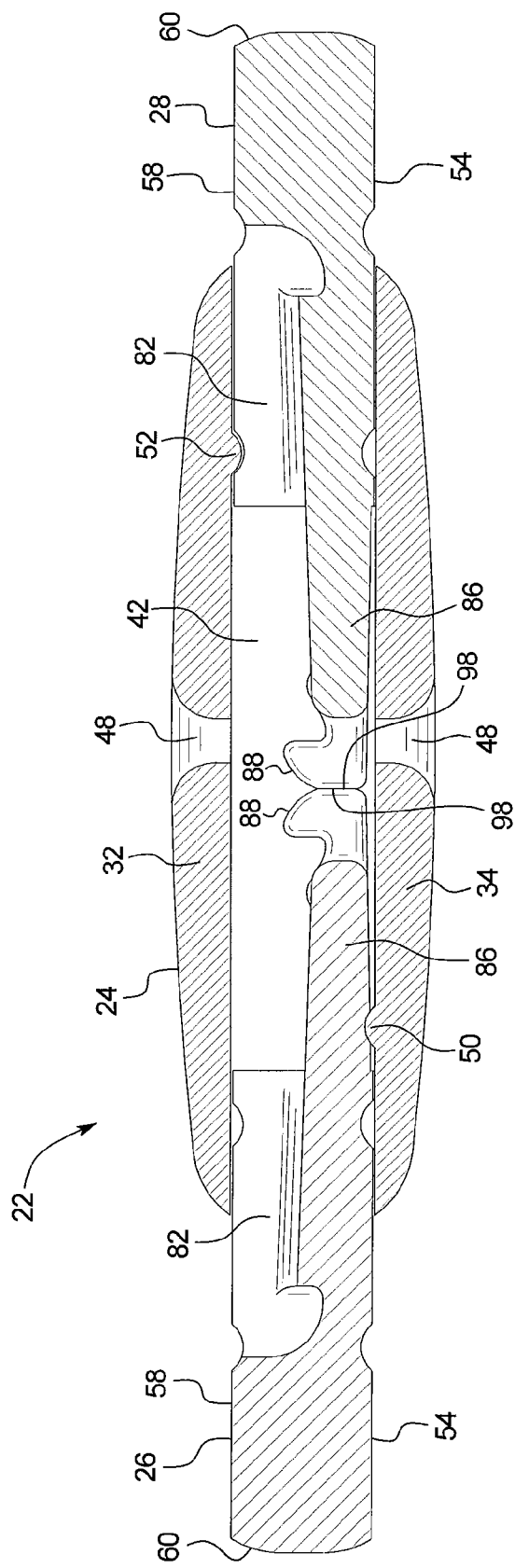
FIG. 16 is a cross-sectional view of the suture retention device with the retention members installed in an incorrect orientation.

As shown in FIG. 16, each of the first and second retention members 26, 28 may also include a vertical surface 98 opposite of the end surface 60. The vertical surface 98 preferably extends at least 30% of the distance between the inner surfaces of the top and bottom walls 32, 34 of the body 24. As a result, the vertical surfaces 98 abut against each other and prevent the first and second retention members 26, 28 from being pushed further into the channel 42 when the first and second retention members 26, 28 are incorrectly installed within the channel 42 so that the top surfaces 54 of the first and second retention members 26, 28 are positioned on the same side of the channel 42.

Figure 17:
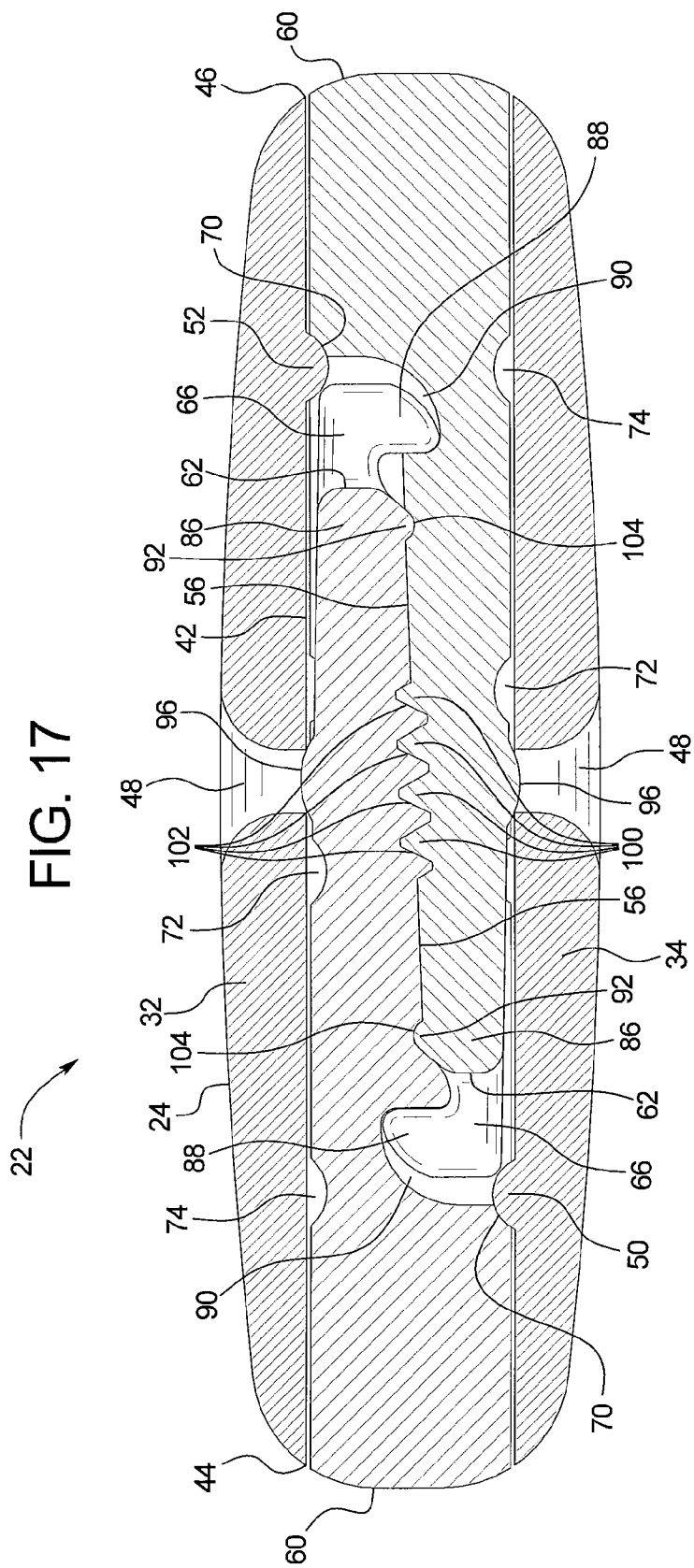
FIG. 17 is a cross-sectional view of another embodiment of the suture retention device, showing the device in the locked state.
Figure 18:
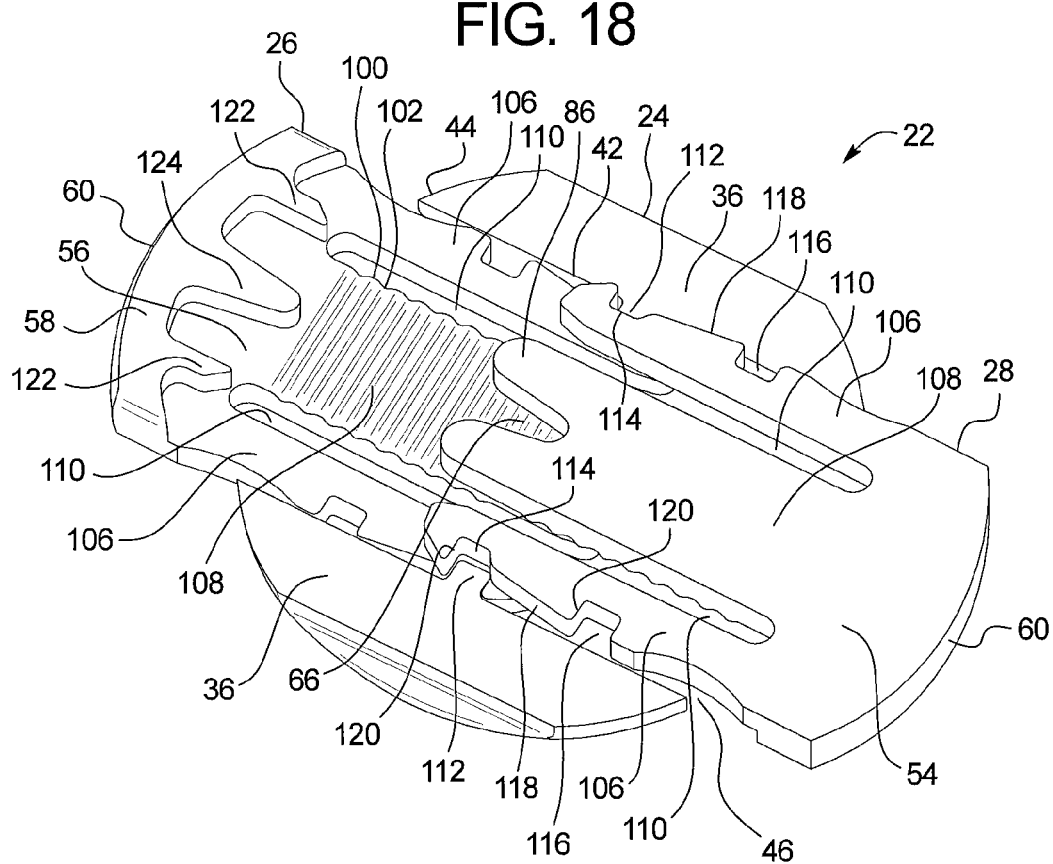
FIG. 18 is a perspective view of another suture retention device with the top wall of the body removed for illustration, showing the device in the unlocked state.

As shown in FIG. 17, each of the first and second retention members 26, 28 may also be provided with a series of protrusions 100 and corresponding recesses 102 along the first bottom surfaces 56 of the first and second retention members 26, 28. As shown in FIG. 18, the protrusions 100 may form ridges 100, and the ridges 100 and recesses 102 may extend across at least a portion of the retention members 26, 28. As shown in FIG. 17, the recesses 102 may mate with the protrusions 100 in the locked state. This arrangement may be useful to increase the force needed to unlock the suture retention device 22. In addition, the protrusions 100 may be sufficiently flexible to flex over the protrusions 100 of the corresponding retention member 26, 28 when the first and second retention members 26, 28 are pushed toward the locked state. This may be useful to increase the force required to push the first and second retention members 26, 28 toward the locked state. The hooks 88 and/or protrusions 100 may also flex over each other when the first and second retention members 26, 28 are pushed toward the locked state. A corresponding recess 104 may also be provided in the first bottom surface 56 of each member 26, 28 for the protrusions 92, which are located adjacent the hooks 88, to mate within in the locked state to increase the unlocking force.

Figure 19:
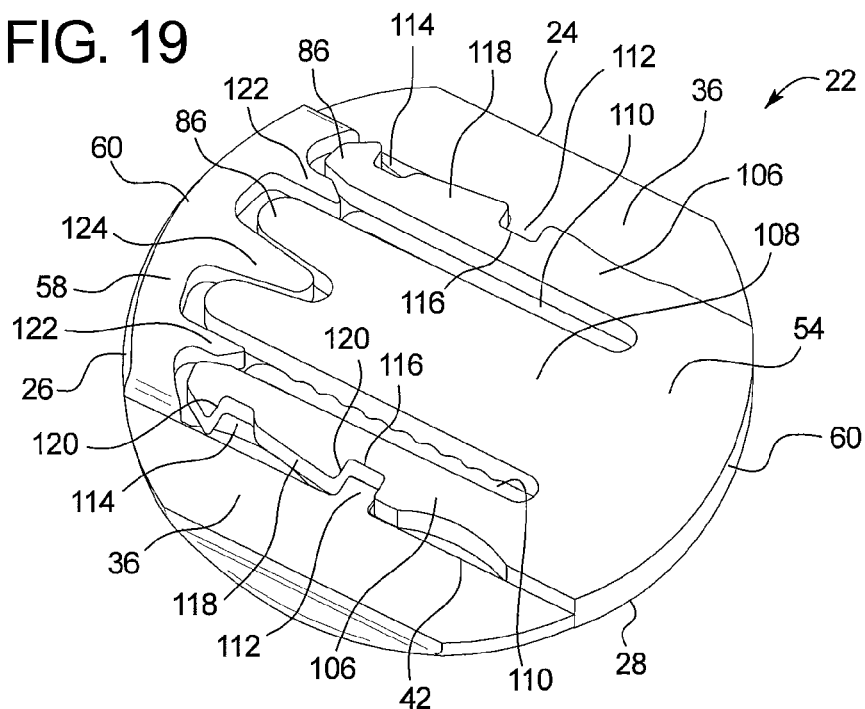
FIG. 19 is a perspective view of the suture retention device, showing the device in the locked state.

As shown in FIGS. 18-19, the first and second retention members 26, 28 may have flexible side arms 106. Each arm 106 is separated from a middle portion 108 of the respective member 26, 28 by a slot 110 extending through the thickness of the member 26, 28 and lengthwise from the end portion 86. The arms 106 are connected to the middle portion 108 at a location opposite from the end portion 86. The channel 42 extending through the body 24 may have protrusions 112, or locking features 112, located on the inner surfaces of the side walls 36. The protrusions 112 may be centered longitudinally within the channel 42. Each of the arms 106 may have a first recess 114 and a second recess 116 that are mateable with the protrusions 112. The first recess 114 is located near the end of an arm 106, and the second recess 116 is located a farther distance from the end of the arm 106.

As shown in FIG. 18, the first recesses 114 mate with the protrusions 112 when the suture retention device 22 is in the unlocked state. Thus, each protrusion 112 engages a first recess 114 of the first retention member 26 and a first recess 114 of the second retention member 28. When the first and second retention members 26, 28 are pushed into the body 24 of the device 22, the protrusions 112 press against an angled side surface 118 of the arms 106 that extends between the first and second recesses 114, 116. As a result, the protrusions 112 gradually flex the arms 106 inward toward the middle portion 108 as the members 26, 28 are pushed into the device 22.

As shown in FIG. 19, when the first and second retention members 26, 28 reach the locked state, the second recesses 116 mate with the protrusions 112 and the arms 106 flex back to their relaxed position. Thus, each protrusion 112 engages a second recess 116 of the first retention member 26 and a second recess 116 of the second retention member 28. Preferably, the protrusions 112 and the recesses 114, 116 have either orthogonal surfaces or acute surfaces 120 on the side 120 nearest the end portion 86 so that the retention members 26, 28 are solidly locked into the body 24 of the device 22 both in the unlocked and locked states to prevent the retention members 26, 28 from being removed from the body 24. If desired, the second bottom surface 58 of each retention member 26, 28 may have portions 122, 124 that extend partially into the slots 110 and partially into the open-ended slot 66. This may be desirable to provide the first and second retention members 26, 28 with increased stability inside of the channel 42 of the body 24.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

We claim:

1. A suture retention device, comprising:

a body comprising a top wall, a bottom wall, a side wall connecting said top and bottom walls, and a channel between said top and bottom walls, said channel extending through said body from a side opening in the body to an opposite side opening in the body, a pair of coaxial holes extending through the top and bottom walls and being in communication with said channel, a locking feature disposed on one or more inner surfaces within said channel between said side opening and said opposite side opening;

first and second retention members each comprising a top surface, a first bottom surface, a second bottom surface, an end surface, a side surface laterally aligned with said coaxial holes disposed away from said end surface and extending through a thickness between said top surface and said first bottom surface, and first and second corresponding locking features longitudinally spaced apart from each other;

said suture retention device comprising an unlocked state wherein said first retention member extends through said side opening and said top surface of said first retention member engages said inner surface of said top wall of said body and said second bottom surface of said first retention member engages said inner surface of said bottom wall, said locking feature of said body and said first corresponding locking feature of said first retention member receive each other, said end surface of said first retention member is disposed outside of said channel, and said side surface of said first retention member is disposed between said end surface of said first retention member and said coaxial holes of said body, and wherein said second retention member extends through said opposite side opening and said top surface of said second retention member engages said inner surface of said bottom wall of said body and said second bottom surface of said second retention member engages said inner surface of said top wall, said locking feature of said body and said second corresponding locking feature of said second retention member receive each other, said end surface of said second retention member is disposed outside of said channel, and said side surface of said second retention member is disposed between said end surface of said second retention member and said coaxial holes of said body; and said suture retention device comprising a locked state wherein said first and second retention members are slid through said channel towards each other by pushing said end surfaces of said first and second retention members toward said side openings of said body such that said locking feature of said body and said first corresponding locking features of said first and second retention members disengage from each other, said locking feature of said body and said second corresponding locking features of said first and second retention members receive each other, said side surfaces of said first and second retention members pass by said coaxial holes of said body to pull a suture extending through said coaxial holes through said channel and away from said coaxial holes, and portions of said first and second retention members overlie each other with said first bottom surfaces of said first and second retention members facing each other within said channel at said coaxial holes.

2. The suture retention device according to claim 1, wherein said locking feature of said body comprises a first locking feature disposed on an inner surface of said top wall or an inner surface of said bottom wall between said side opening and said coaxial holes and a second locking feature disposed on an inner surface of said top wall or an inner surface of said bottom wall between said opposite side opening and said coaxial holes, said first and second corresponding locking features being disposed on said top surface or said second bottom surface of said first and second retention members.

3. The suture retention device according to claim 2, wherein each of said first and second retention members comprise third and fourth corresponding locking features disposed on the opposite top surface or second bottom surface from said first and second corresponding locking features, said third and fourth corresponding locking features receiving said first and second locking features of said body in said unlocked and locked states in place of said first and second corresponding locking features when said first and second retention members are incorrectly installed within said channel with said top surface of said first retention member engaging said inner surface of said bottom wall and said top surface of said second retention member engaging said inner surface of said top wall.

4. The suture retention device according to claim 1, wherein said locking feature of said body is disposed on an inner surface of said side wall and is longitudinally centered within said channel, said locking feature being at least a single locking feature that receives both said first corresponding locking feature of said first retention member and said first corresponding locking feature of said second retention member in said unlocked state, and receives both said second corresponding locking feature of said first retention member and said second corresponding locking feature of said second retention member in said locked state, said first and second corresponding locking features being disposed on flexible arms of said first and second retention members, each of said flexible arms being separated from a middle portion of said first and second retention members by a slot.

5. The suture retention device according to claim 1, wherein said first and second retention members each comprise a series of protrusions and recesses on said first bottom surfaces, said recesses of said first retention member receiving said protrusions of said second retention member and said recesses of said second retention member receiving said protrusions of said first retention member in said locked state.

6. The suture retention device according to claim 1, wherein said body comprises two said side walls enclosing said channel, said two side walls defining a width therebetween corresponding to a width of each of said first and second retention members, said width between said side walls thereby guiding said first and second retention members as said first and second retention members are pushed from said unlocked state to said locked state.

7. The suture retention device according to claim 1, wherein said end surfaces are generally aligned with said side openings of said body in said locked state.

8. The suture retention device according to claim 1, wherein each of said side surfaces of said first and second retention members is a portion of an open-ended slot.

9. The suture retention device according to claim 1, wherein each of said first and second retention members comprises an end portion opposite from said end surface and a recessed portion between said end portion and said end surface defined by side walls, said side walls defining said second bottom surface of each of said first and second retention members, and each of said end portions extends into said recessed portion of the other retention member in said locked position.

10. The suture retention device according to claim 9, wherein each of said first and second retention members comprises a recess in said first bottom surface, each of said hooks being received by said recess in the other first and second retention member in said locked state.

11. The suture retention device according to claim 10, wherein each of said protrusions of said first and second retention members comprise a ridge extending across each of said first and second retention members, a recess laterally aligned with said coaxial holes extending through each of said ridges.

12. The suture retention device according to claim 9, wherein each of said first and second retention members comprises a protrusion extending from said first bottom surfaces of said first and second retention members, said protrusions causing said hooks of said first and second retention members to flex over said protrusions when said first and second retention members are pushed toward said locked state.

13. The suture retention device according to claim 1, wherein each of said first and second retention members comprises a hook along an end portion opposite from said end surface, said hook of said first retention member extending toward said inner surface of said bottom wall of said body and said hook of said second retention member extending toward said inner surface of said top wall of said body, said hooks engaging each other in said unlocked state.

14. The suture retention device according to claim 1, wherein each of said first and second retention members comprises a vertical surface opposite of said end surface, said vertical surface extending at least 30% of a distance between said inner surfaces of said top and bottom walls of said body, said vertical surfaces thereby abutting against each other and preventing said first and second retention members from being further pushed into said channel when said first and second retention members are incorrectly installed within said channel with said top surfaces of said first and second retention members disposed on the same side of said channel.

15. The suture retention device according to claim 1, wherein each of said first and second retention members comprises a protrusion extending from said top surfaces, each of said protrusions extending at least partially into one of said coaxial holes in said locked state.

16. The suture retention device according to claim 1, wherein said locking feature of said body comprises a protrusion extending across said channel and each of said first and second corresponding locking features of said first and second retention members comprises a recess extending across each of said first and second retention members.

17. The suture retention device according to claim 1, further comprising a retention wire extending through said coaxial holes in said unlocked state.

18. The suture retention device according to claim 17, wherein said retention wire comprises a first end larger in size than said coaxial holes disposed above said top wall of said body and a second end smaller in size than said coaxial holes disposed below said bottom wall of said body, said retention wire being withdrawable by pulling said first end away from said top wall but not being withdrawable by pulling said second end away from said bottom wall.

19. The suture retention device according to claim 18, wherein said second end of said retention wire comprises a cross hole through the second end disposed below said bottom wall.

20. The suture retention device according to claim 1, wherein said body comprises two said side walls enclosing said channel, said two side walls defining a width therebetween corresponding to a width of each of said first and second retention members, said width between said side walls thereby guiding said first and second retention members as said first and second retention members are pushed from said unlocked state to said locked state, said end surfaces are generally aligned with said side openings of said body in said locked state, each of said side surfaces of said first and second retention members is a portion of an open-ended slot, each of said side surfaces is a portion of a circular surface in alignment with said coaxial holes in said unlocked state.

* * * * *